United States Patent [19]

Kamei et al.

[11] Patent Number: 5,196,406
[45] Date of Patent: Mar. 23, 1993

[54] CYCLODEXTRIN COMPLEX OF FUMAGILLIN DERIVATIVE

[75] Inventors: Shigeru Kamei, Takarazuka; Hiroaki Okada, Suita; Katsuichi Sudo, Takatsuki; Shoji Kishimoto, Takarazuka, all of Japan

[73] Assignee: Takeda Chemical Industries, Ltd., Osaka, Japan

[21] Appl. No.: 704,347

[22] Filed: May 23, 1991

[30] Foreign Application Priority Data

May 25, 1990 [JP] Japan ................................. 2-136343
Feb. 6, 1991 [JP] Japan ................................. 3-015333

[51] Int. Cl.$^5$ .................... A61K 31/335; A61K 47/40
[52] U.S. Cl. ...................................... 514/58; 514/778; 536/103; 549/356
[58] Field of Search ................ 514/58, 778; 549/356; 536/103

[56] References Cited

U.S. PATENT DOCUMENTS

| | | | |
|---|---|---|---|
| 3,260,714 | 7/1966 | Schroeder | 536/16.5 |
| 3,418,414 | 12/1968 | Houtman | 536/16.5 |
| 3,448,097 | 6/1969 | Argoudelis | 536/16.5 |
| 3,856,943 | 12/1974 | Birkenmeyer | 536/16.5 |
| 4,278,789 | 7/1981 | Birkenmeyer | 536/16.5 |
| 4,310,660 | 1/1982 | Birkenmeyer | 536/16.5 |
| 4,383,109 | 5/1983 | Argoudelis et al. | 536/16.2 |
| 4,457,916 | 7/1984 | Hayashi et al. | 424/85.1 |
| 4,568,741 | 2/1986 | Livingston | 536/16.5 |
| 4,869,904 | 9/1989 | Uekama et al. | 514/58 |
| 4,983,586 | 1/1991 | Bodor | 514/58 |
| 5,019,562 | 5/1991 | Folkman et al. | 514/58 |
| 5,070,081 | 12/1991 | Majid et al. | 514/58 |
| 5,079,237 | 1/1992 | Husu et al. | 514/58 |

FOREIGN PATENT DOCUMENTS

| | | |
|---|---|---|
| 0094157 | 11/1983 | European Pat. Off. . |
| 0325199 | 7/1989 | European Pat. Off. . |
| 0354767 | 2/1990 | European Pat. Off. . |
| 0354787 | 2/1990 | European Pat. Off. . |
| 0357061 | 3/1990 | European Pat. Off. . |
| 0359036 | 3/1990 | European Pat. Off. . |
| 0415294 | 3/1991 | European Pat. Off. . |
| WO89/06536 | 7/1989 | PCT Int'l Appl. . |

OTHER PUBLICATIONS

K. Uekama, *Yakugaku Zasshiii*, vol. 101(10), pp. 857-873 (1981).
D. Duchene et al., *Pharmaceutical Technology*, pp. 26, 28, 32 and 34 (1990).

*Primary Examiner*—Ronald W. Griffin
*Attorney, Agent, or Firm*—David G. Conlin; Gregory D. Williams; Peter F. Corless

[57] ABSTRACT

A complex of a fumagillin derivative represented by the general formula:

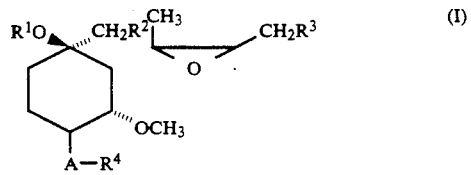

wherein $R^1$ is hydrogen; $R^2$ is halogen, $N(O)mR^5R^6$, $N^+R^5R^6R^7.X^-$, $S(O)nR^5$ or $S^+R^5R^6.X^-$ (wherein $R^5$, $R^6$ and $R^7$ are independently an optionally substituted hydrocarbon or heterocyclic group; $X^-$ is a counter anion; m is an integer of 0 or 1; n is an integer from 0 to 2; and $R^5$ and $R^6$ together with the adjacent nitrogen or sulfur atom may form a nitrogen- or sulfur-containing heterocyclic group which may be substituted and form a condensed ring); or $R^1$ and $R^2$ together represent a bond; $R^3$ is 2-methyl-1-propenyl group or isobutyl group; A is O or $NR^8$ (wherein $R^8$ is hydrogen or an optionally substituted lower alkyl or aryl group); $R^4$ is hydrogen, an optionally substituted hydrocarbon group or an optionally substituted acyl group); or a salt thereof, with an optionally etherified cyclodextrin is disclosed. The present invention also provides an antineoplastic agent containing the complex.

32 Claims, No Drawings

CYCLODEXTRIN COMPLEX OF FUMAGILLIN DERIVATIVE

FIELD OF THE INVENTION

The present invention relates to a cyclodextrin complex of a fumagillol derivative or a salt thereof. The complex of the present invention increases the water-solubility of a fumagillol derivative or a salt thereof and promotes its absorption and further enhances its pharmacological activities. Fumagillol derivatives have been shown to have vascularization inhibition activity, and are useful for treatment and prevention of various inflammatory diseases (rheumatic diseases, psoriasis, etc.), diabetic retiopathy or tumors.

BACKGROUND OF THE INVENTION

Angiogenesis is concerned with the occurrence or pathological processes of various inflammatory diseases (rheumatic diseases, psoriasis, etc.) diabetic retinopathy, tumors, and the like. Therefore, it has been considered that inhibition of angiogenesis or vascularization has a connection with the therapy and prophylaxis of such diseases. A number of research groups have searched for compositions which prevent or inhibit vascularization. For example, EP-A-359,036, EP-A-357,061, EP-A-354,787, EP-A-386,667 and EP-A-415,294 disclose that fumagillol derivatives have excellent vascularization inhibition activity and they also disclose processes for the production thereof. Some of these fumagillol derivatives have low water-solubility. Accordingly, it is desirable to obtain suitable means for enhancing water-solubility to facilitate administration and to obtain more effective pharmacological activity.

OBJECTS OF THE INVENTION

The main object of the present invention is to enhance water-solubility of fumagillol derivatives which have vascularization inhibition activity and thereby increase their pharmacological activity.

SUMMARY OF THE INVENTION

Under these circumstances, the present inventors have studied intensively how to enhance the water-solubility of fumagillol derivatives. As a result, it has been surprisingly found that the water-solubility of a fumagillol derivative can be increased by forming a novel complex of a fumagillol derivative with an optionally etherified cyclodextrin which has never been used in the field of fumagillol derivatives.

That is, the present invention provides a cyclodextrin complex of a fumagillol derivative, wherein the fumagillol derivative portion of the complex is represented by the general formula:

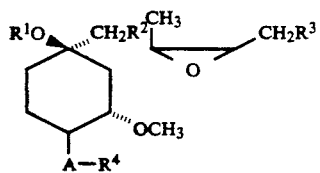
(I)

wherein $R^1$ is hydrogen; $R^2$ is halogen, $N(O)mR^5R^6$, $N^+R^5R^6R^7 \cdot X^-$, $S(O)nR^5$ or $S^+R^5R^6 \cdot X^-$ (wherein $R^5$, $R^6$ and $R^7$ are independently an optionally substituted hydrocarbon or heterocyclic group; $X^-$ is a counter anion; m is an integer of 0 or 1; n is an integer from 0 to 2; and $R^5$ and $R^6$ together with the adjacent nitrogen or sulfur atom may form a nitrogen- or sulfur-containing heterocyclic group which may be substituted and form a condensed ring); or $R^1$ and $R^2$ together represent a bond; $R^3$ is 2-methyl-1-propenyl group or isobutyl group; A is O or $NR^8$ (wherein $R^8$ is hydrogen or an optionally substituted lower alkyl or aryl group); $R^4$ is hydrogen, an optionally substituted hydrocarbon group or an optionally substituted acyl group); or a salt thereof, with an optionally etherified cyclodextrin. The present invention also provides an antineoplastic agent containing the complex.

DETAILED DESCRIPTION OF THE INVENTION

In the above general formula (I), halogen represented by $R^2$ includes fluorine, chlorine, bromine and iodine. When $R^1$ and $R^2$ together represent a bond, an epoxy ring is formed.

The hydrocarbon group of the optionally substituted hydrocarbon group represented by $R^5$, $R^6$ and $R^7$ includes a straight or branched chain $C_{1-6}$ alkyl (e.g., methyl, ethyl, propyl, ispropyl, butyl, isobutyl, secbutyl, pentyl, isopentyl, hexyl, etc.), $C_{2-6}$ alkenyl (e.g., vinyl, allyl, 2-butenyl, methylally, 3-butenyl, 2-pentenyl, 4-pentenyl, 5-hexenyl, etc.), C2-6 alkynyl (e.g., ethynyl, propargyl, 2-butyn-1-yl, 3-butyn-2-yl, 1-pentyn-3-yl, 3-pentyn-1-yl, 4-pentyn-2-yl, 3-hexyn-1-yl, etc.), $C_{3-6}$ cycloalkyl (e.g., cyclopropyl, cyclobutyl, cyclopentyl, cyclohexyl, etc.), $C_{3-6}$ cycloalkenyl (e.g., cyclobutenyl, cyclopentenyl, cyclohexenyl, cyclohexadienyl, etc.), $C_{7-13}$ aralkyl (e.g., benzyl, 1-phenethyl, 2-phenethyl, etc.), and $C_{6-10}$ aryl (e.g., phenyl, naphthyl, etc.).

The heterocyclic group of the optionally substituted heterocyclic group represented by $R^5$, $R^6$ and $R^7$ includes a 5- or 6-membered heterocyclic group containing 1 to 4 hetero atoms (e.g., nitrogen, oxygen, sulfur, etc.), for example, 2-furyl, 2-thienyl, 4-thiazolyl, 4-imidazolyl, 4-pyridyl, 1,3,4-thiadiazol-2-yl, 1-methyl-5-tetrazolyl or the like. Further, the heterocyclic group may be condensed with 5- or 6-membered ring (e.g., benzene, pyridine, cyclohexane, etc.) to form bicyclic group (e.g., 8-quinolyl, 8-purinyl, etc.).

The nitrogen-containing heterocyclic group which may be formed by $R^5$ and $R^6$ together with the adjacent nitrogen atom includes a 4- to 7-membered nitrogen-containing heterocyclic group (e.g., pyrrolidin-1-yl, piperazino, morpholino, 4-methylpiperazin-1-yl, etc.).

The sulfur-containing heterocyclic group which may be formed by $R^5$ and $R^6$ together with the adjacent nitrogen atom includes a 4- to 7-membered sulfur-containing heterocyclic group (e.g., tetrahydrothiophen-1-yl, 1,4-thioxan-1-yl, etc.).

The nitrogen- or sulfur-containing heterocyclic group which may be formed by $R^5$ and $R^6$ together with the adjacent nitrogen or sulfur atom may be condensed with 5 or 6-membered group (e.g., benzene, pyridine, pyrazine, pyridazine, cyclohexane, etc.) to form bicyclic group (e.g., isoindolin-2-yl, 2-isoquinolyl, 1,3-dihydrobenzo[c]thiophen-2-yl, 2,3-dihydrobenzo[b]thiophen-1-yl, 3,4-dihydro-1H-2-benzopyran-2-yl, 3,4-dihydro-2H-1-benzopyran-1-yl, 1,2,4,5-tetrahydro-3-benzothiepin-3-yl, 1,3-dihydrothieno[3,4-c]pyridin-2-yl, 5,7-dihydrothieno[3,4-b]pyrazin-6-yl, 5,7-dihydrothieno[3,4-d]pyridazin-6-yl, etc.).

The lower alkyl group of the optionally substituted lower alkyl group represented by $R^8$ includes a $C_{1-6}$ alkyl group (e.g., methyl, ethyl, propyl, isopropyl, butyl, isobutyl, sec-butyl, pentyl, isopentyl, hexyl, etc.).

The aryl group of the optionally substituted aryl group represented by $R^8$ includes a $C_{6-10}$ aryl group (e.g., phenyl, naphthyl, etc.).

The hydrocarbon group of the optionally substituted hydrocarbon group by $R^4$ includes those described above with respect to the optionally substituted hydrocarbon represented by $R^5$, $R^6$ and $R^7$.

When the hydrocarbon represented by $R^4$ is an alkenyl group, preferably, it does not have any substituent.

The optionally substituted acyl group represented by $R^4$ includes residues of optionally substituted acids such as carboxylic acid acyl, sulfonic acid acyl, carbamoyl, thiocarbamoyl and sulfamoyl which may have substituents (an acyl group derived from the corresponding acid). For example, they are alkanoyl, aroyl, heterocyclic carbonyl, carbamoyl, thiocarbamoyl, arylsulfonyl, alkylsulfonyl, sulfamoyl, alkoxycarbonyl, aryloxycarbonyl and the like which may have substituents.

The alkanoyl group of the above optionally substituted alkanoyl group includes a $C_{1-6}$ alkanoyl group (e.g., formyl, acetyl, propionyl, isopropionyl, butyryl, pentanoyl, hexanoyl, etc.).

The aroyl group of the optionally substituted aroyl group includes a $C_{7-11}$ aroyl group (e.g., benzoyl, 1-naphthoyl, 2-naphthoyl, etc.).

The heterocyclic carbonyl group of the optionally substituted heterocyclic carbonyl group includes a 5- or 6-membered heterocyclic carbonyl group containing 1 to 4 hetero atoms (e.g., nitrogen, oxygen, sulfur, etc.), for example, 2-furoyl, 2-thenoyl, nicotinyl, isonicotinyl and the like.

The arylsulfonyl group of the optionally substituted arylsulfonyl group includes a $C_{6-10}$ arylsulfonyl group (e.g., benzenesulfonyl, 1-naphthylsulfonyl, 2-naphthylsulfonyl, etc.).

The alkylsufonyl group of the optionally substituted alkylsulfonyl group includes a $C_{1-6}$ alkylsulfonyl group (e.g., methylsulfonyl, ethylsulfonyl, etc.).

The alkoxycarbonyl group of the optionally substituted alkoxycarbonyl group includes a $C_{2-7}$ alkoxycarbonyl group (e.g., methoxycarbonyl, ethoxycarbonyl, isobutoxycarbonyl, etc.).

The aryloxycarbonyl group of the optionally substituted aryloxycarbonyl group includes a $C_{7-11}$ aryloxycarbonyl group (e.g., phenoxycarbonyl, 1-naphthyloxycarbonyl, 2-naphthyloxycarbonyl, etc.).

The optionally substituted hydrocarbon or heterocyclic group represented by $R^5$, $R^6$ and $R^7$; the optionally substituted nitrogen- or sulfur-containing heterocyclic group formed by $R^5$ and $R^6$ together with the adjacent nitrogen or sulfur atom which may be condensed with a further ring; the optionally substituted lower alkyl or aryl group represented by $R^8$; as well as the optionally substituted hydrocarbon group and the optionally substituted acyl group (alkanoyl, aroyl, heterocyclic carbonyl, carbamoyl, thiocarbamoyl, arylsulfonyl, alkylsulfonyl, sulfamoyl, alkoxycarbonyl, or aryloxycarbonyl) represented by $R^4$ may contain 1 to 3 substituents at the possible positions.

Such substituents include, for example, a $C_{1-6}$ alkyl group (e.g., methyl, ethyl, propyl, isopropyl, butyl, isobutyl, sec-butyl, pentyl, isopentyl, hexyl, etc.), a $C_{2-6}$ alkenyl group (e.g., vinyl, allyl, 2-butenyl, methylallyl, 3-butenyl, 2-pentenyl, 4-pentenyl, 5-hexenyl, etc.), a $C_{2-6}$ alkynyl group (e.g., ethynyl, propargyl, 2-butyn-1-yl, 3-butyn-2-yl, 1-pentyn-3-yl, 3-pentyn-1-yl, 4-pentyn-2-yl, 3-hexyn-1-yl, etc.), a $C_{3-6}$ cycloalkyl group (e.g., cyclopropyl, cyclobutyl, cyclopentyl, cyclohexyl, etc.), a $C_{3-6}$ cycloalkenyl group (e.g., cyclobutenyl, cyclopentenyl, cyclohexenyl, cyclohexadienyl, etc.), a $C_{6-10}$ aryl group (e.g., phenyl, naphthyl, etc.), amino, a $C_{1-6}$ alkylamino group (e.g, methylamino, ethylamino, isopropylamino, etc.), di- $C_{1-6}$ alkylamino group (e.g., dimethylamino, diethylamino, etc.), azido, nitro, halogen (e.g., fluorine, chlorine, bromine, iodine, etc.), hydroxyl, a $C_{1-4}$ alkoxy group (e.g., methoxy, ethoxy, etc.), a $C_{6-10}$ aryloxy group (e.g., phenoxy, naphthyloxy, etc.), a $C_{1-6}$ alkylthio group (e.g., methylthio, ethylthio, propylthio, etc.), a $C_{6-10}$ arylthio group (e.g., phenylthio, naphthylthio, etc.), cyano, carbamoyl, carboxyl, a $C_{1-4}$ alkoxycarbonyl group (e.g., methoxycarbonyl, ethoxycarbonyl, etc.), a $C_{7-11}$ aryloxycarbonyl group (e.g., phenoxycarbonyl, 1-naphthyloxycarbonyl, 2-naphthyloxycarbonyl, etc.), a carboxy - $C_{1-4}$ alkoxy group (e.g., carboxymethoxy, 2-carboxyethoxy, etc.), a $C_{1-6}$ alkanoyl group (e.g., formyl, acetyl, propionyl, butyryl, pentanoyl, hexanoyl, etc.), a $C_{7-11}$ aroyl group (e.g., benzoyl, 1-naphthoyl, 2-naphthoyl, etc.), a $C_{6-10}$ arylsulfonyl group (e.g., benzenesulfonyl, 1-naphthylsulfonyl, 2-naphthylsulfonyl, etc.), a $C_{1-6}$ alkylsulfinyl group (e.g., methylsulfinyl, ethylsulfinyl, etc.), a $C_{6-10}$ arylsulfinyl group (e.g., benzenesulfinyl, 1-naphthylsulfinyl, 2-naphthylsulfinyl, etc.), a $C_{1-6}$ alkylsulfonyl group (e.g., methylsulfonyl, ethylsulfonyl, etc.), 5- or 6-membered heterocyclic group containing 1 to 4 hetero atoms (e.g., nitrogen, oxygen, sulfur, etc.) (e.g., furyl, 2-thienyl, 4-thiazolyl, 4-imidazolyl, 4-pyridyl, 1,3,4-thiadiazol-2-yl, 1-methyl-5-tetrazolyl, etc.), 5- or 6-membered heterocyclic carbonyl group containing 1 to 4 hetero atoms (e.g., nitrogen, oxygen, sulfur, etc.) (e.g., furoyl, 2-thenoyl, nicotinyl, isonicotinyl, etc.), 5- or 6-membered heterocyclic thio group containing 1 to 4 hetero atoms (e.g., nitrogen, oxygen, sulfur, etc.) (e.g., 4-pyridylthio, 2-pyrimidylthio, 1,3,4-thiadiazol-2-ylthio, 1-methyl-5-tetrazolylthio, etc.) and the like. Further, the heterocyclic thio group may be condensed with benzene ring to form a condensed bicyclic thio group (e.g., 2-benzothiozolylthio, 8-quinolythio, etc.). Alternatively, when $R^4$ represents disubstituted carbamoyl, thiocarbamoyl or sulfamoyl group, the substituents together with the nitrogen atom of the carbamoyl, thiocarbamoyl, or sulfamoyl group may form a nitrogen-containing heterocyclic group (e.g., pyrrolidin-1-yl, piperidino, morpholino, piperazin-1-yl, 4-methylpiperazin-1-yl, 4-phenylpiperazin-1-yl, etc.).

The substituent in the optionally substituted hydrocarbon or heterocyclic group represented by $R^5$, $R^6$ and $R^7$; the substituent in the nitrogen- or sulfur-containing heterocyclic group which may be formed by $R^5$ and $R^6$ together with the adjacent nitrogen or sulfur atom and may be condensed with a further ring: the substituent in the optionally substituted lower alkyl group or aryl group represented by $R^8$; as well as the substituent in the optionally substituted hydrocarbon group and optionally substituted alkanoyl, aroyl, heterocyclic carbonyl, carbamoyl, thiocarbamoyl, arylsulfonyl, alkylsulfonyl, sulfamoyl, alkoxycarbonyl, aryloxycarbonyl or aryloxycarbonyl group represented by $R^4$ may further contain 1 to 3 substituents in the possible positions.

Examples of such substituents include the aforementioned $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-10}$ aryl group, amino, $C_{1-6}$ alkylamino group, di-$C_{1-6}$ alkylamino group, azido, nitro, halogen, hydroxyl, $C_{1-4}$ alkoxy group, $C_{6-10}$ aryloxy group, $C_{1-6}$ alkylthio group, $C_{6-10}$ arylthio group, cyano, carbamoyl, carboxyl, $C_{1-4}$ alkoxylcarbonyl group, $C_{7-11}$ aryloxycarbonyl group, carboxy - $C_{1-4}$ alkoxy group, $C_{1-6}$ alkanoyl group, $C_{7-11}$ aroyl group, $C_{6-10}$ arylsulfonyl group, $C_{1-6}$ alkylsulfinyl group, $C_{6-10}$ arylsulfinyl group, $C_{1-6}$ alkylsulfonyl group, 5- or 6-membered heterocyclic group, 5- or 6-membered heterocyclic carbonyl group and 5- or 6-membered heterocyclic thio group.

The counter anion represented by $X^-$ includes, for example, halogen ion (e.g., iodide ion, bromide ion, chloride ion, etc.), sulfate ion, phosphate ion, nitrate ion, perchlorate ion, tetrafluoroborate ion, methanesulfate ion, p-tolylsulfate ion, benzenesulfate ion, hydroxyl ion, organic carboxylate ion (e.g., oxalate ion, maleate ion, fumarate ion, succinate ion, citrate ion, lactate ion, trifluoroacetate ion, lactobionate ion, acetate ion, propionate ion, tartrate ion, ethyl succinate ion, etc.).

The compound (I) has an asymmetric center in its molecule and is optically active. Its absolute configuration is derived from the starting material, fumagillol. When the configuration is shown, the absolute configuration is the same as that of fumagillol. The mode of bonding of the substituents on the cyclohexane ring is as follows: ..., __, and —, represent $\alpha$ bond, $\beta$ bond, and either $\alpha$ or $\beta$ bond, respectively.

When the compound (I) has an acidic substituent (e.g., carboxyl, etc.) or a basic substituent (e.g., amino, lower alkylamino, di-lower alkylamino, nitrogen-containing heterocyclic group, etc.), it may be used as a physiologically acceptable salt thereof. Examples of the physiologically acceptable salt include those with inorganic bases, inorganic acids, organic bases, organic acids and basic or acidic amino acids. As the inorganic base which can produce these salts, there are, for example, alkali metal (e.g., sodium, potassium, etc.) and alkaline earth metal (e.g., calcium, magnesium, etc.); as the organic base, there are, for example, trimethylamine, triethylamine, pyridine, picoline, N,N-dibenzylethylenediamine, ethanolamine, diethanolamine, tris(hydroxymethyl)- aminomethane, dicyclohexylamine, etc.; as the inorganic acid, there are, for example, hydrochloric acid, hydrobromic acid, sulfuric acid, nitric acid, phosphoric acid; as the organic acid, there are, for example, formic acid, acetic acid, trifluoroacetic acid, oxalic acid, tartaric acid, fumaric acid, maleic acid, methanesulfonic acid, benzenesulfonic acid, p-toluenesulfonic acid, etc.; and as the basic or acidic amino acid, there are, for example, arginine, lysine, ornithine, aspartic acid, glutamic acid, etc. Among these salts, those with bases (i.e., salts with inorganic bases, salts with organic bases, salts with basic amino acids) indicate those formed with carboxyl group in the substituent of the compound (I), or salts with acids (i.e., salts with inorganic acids, salts with organic acids, salts with acidic amino acids) indicate those which can be formed with amino, lower alkylamino group, di-lower alkylamino group, nitrogen-containing heterocyclic group, di-lower alkylamino group, nitrogen-containing heterocyclic group or the like in the substituent of the compound (I).

When the compound (I) has a di-lower alkyl amino group, a nitrogen-containing heterocyclic group or a nitrogen-containing aromatic heterocyclic group, the nitrogen atom in these substituents may be further alkylated to form a quaternary ammonium group (e.g., trimethylammonium, N-methylpyridinium, N-methylpyrrolidin-1-ylium, etc.), and the counter anion thereof includes those shown with respect to the aforementioned counter anion represented by $X^-$.

In the compound (I), preferably, $R^1$ and $R^2$ together represent a bond, or $R^1$ is hydrogen and $R^2$ is $N(O)mR^5R^6$, $N^+R^5R^6R^7 \cdot X^-$, $S(O)nR^5$ and $S^+(O)MR^5R^6 \cdot X^-$. Particularly, $R^2$ is $S^+R^5R^6 \cdot X^-$ wherein $R^5$ and $R^6$ are hydrocarbon group, and $X^-$ is halogen is preferred.

A is preferably O or NH. $R^3$ is preferably 2-methyl-1-propenyl and $R^4$ is preferably a substituted carbamyl.

The compound represented by the general formula (I) or a salt thereof can be produced by using fumagillol [Tarbell, D. S. et. al., J. Am. Chem. Soc., 83, 3096 (1961)], a hydrolyzate of fumagillin produced by a microorganism as a starting material, and the production process as well as physical and biological properties thereof are described in detail in the aforementioned patent publications.

The optionally etherified cyclodextrin to be used in the present invention (hereinafter abbreviated to CyD) indicates a cyclic oligosaccharide composed of 6 to 12 glucose units wherein hydroxyl groups at 2-, 3- and 6-positions may be partly or totally substituted with other functional groups.

The examples of the CyD include a compound represented by the general formula:

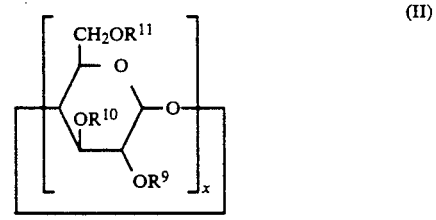

wherein x is an integer of 6 to 12; and $R^9$, $R^{10}$ and $R^{11}$ are independently hydrogen, alkyl, monohydroxyalkyl, dihydroxyalkyl, carboxyalkyl or a sugar residue, and $R^9$, $R^{10}$ and $R^{11}$ in respective repetition units are the same or different. Examples thereof include $\alpha$-CyD (x=6), $\beta$-CyD (x=7), $\gamma$-CyD (x=8), $\delta$-CyD (x=9) and their derivative having etherified hydroxyl group.

As the alkyl group represented by $R^9$ to $R^{11}$, there are, for example, $C_{1-4}$ alkyl such as methyl, ethyl, propyl: as monohydroxylalkyl, there are, for example, monohydroxy-$C_{1-4}$ alkyl such as hydroxymethyl, 2-hydroxyethyl; as dihydroxyalkyl, there are, for example, dihydroxy-$C_{1-4}$ alkyl such as dihydroxymethyl, 2,2-dihydroxyethyl; as carboxyalkyl, there are, for example, carboxy - $C_{1-4}$ alkyl such as carboxymethyl; 2-carboxymethyl; as the sugar residue, there are, for example, glucosyl, maltosyl, panosyl and the like.

These CyD may be used alone or in combination thereof. The amount of the CyD to be used depends on a particular combination of the compound (I) or a salt thereof and the compound (II) and, normally, the amount thereof is selected so that the amount of CyD is 1/10 to 50 times (by weight), particularly, 1/5 to 20 times (by weight), more preferably 1 to 10 times (by weight) that of the compound (I) or a salt thereof.

Normally, the complex of the present invention is produced, for example, by dissolving the cyclodextrin (II) in water, adding the compound (I) or a salt thereof with stirring at a temperature from about $-10°$ C. to 35° to about 80° C. Optionally, additional steps such as the filtration, lyophilization and additional steps such as the filtration, lyophilization and addition of organic solvent can be conducted to obtain a powder product.

In the product thus obtained, it is believed that a complex which is a clathrate compound or a complex formed by electrostatic or hydrophobic interaction of hydrogen bond may be present. In the present invention, the term "complex" means such a complex itself as well as a mixture of the complex, a free fumagillol derivative, a salt thereof and/or a free CyD.

The complex of the present invention can be directly administered as a conventional injection preparation intramuscularly, subcutaneously, intravascularly, or to the organ or focus such as tumor. It can be formed into various release controlled preparations, target-directing preparations according to the conventional methods, and it can be used as the raw material for producing such preparations.

The conventional additives such as preservatives, stabilizers, agents for making isotonic can be added to the complex of the present invention.

Further, according to conventional methods, the complex of the present invention can be formed into preparations other than injection preparations, for example, preparations administered to the mucous membranes such as nasal, oral rectal vaginal, uterine mucous membranes, percutaneous preparations or implantation preparations which can be directly applied to the tumor portion or the portion after the tumor is excised.

The complex of the present invention is less toxic and manifests strong antineoplastic activity, and is useful as an antineoplastic agent for mammals (e.g., monkey, cattle, dog, human being, et c.).

For example, for treatment of adult patient suffering from cancer, 1.0 mg to 1.0 g, preferably, 50 mg to 1.0 g of the complex of the present invention is administered orally or parenterally in 1 to 3 times per day.

The following examples further illustrate the present invention in detail but are not to be construed to limit the scope thereof.

EXAMPLE 1

Five milligrams of 6-O-(N-chloroacetylcarbamoyl)-fumagillol was added to 5, 10 or 20 mg of α- or β-cyclodextrin (α-CyD or β-CyD) dissolved in distilled water and the mixture was stirred at room temperature (15 to 25° C.). After 4 hours, the mixture was filtered through a filter (0.22 μm in pore diameter) and the fumagillol compound obtained in the filtrate was quantitatively determined by high performance liquid chromatography (HPLC).

Solubility upon addition of CyD is shown in Table by taking the solubility without addition of CyD as 1.

TABLE 1

| CyD (mg) | Solubility | |
|---|---|---|
| | α-CyD | β-CyD |
| 0 | 1.0 | 1.0 |
| 5 | 2.1 | 2.1 |
| 10 | 2.4 | 2.6 |
| 20 | 3.1 | 2.7 |

EXAMPLE 2

Five milligrams of 6α-(N'-chloroacetylureido)-6-desoxyfumagillol was added to 20 mg of β-CyD dissolved in distilled water (1 ml), and the mixture was stirred at room temperature (15-25° C.). After 4 hours, the mixture was filtered through a filter (0.22 μm in pore diameter) and the fumagillol compound obtained in the filtrate was quantitatively determined by HPLC.

Solubility upon addition of β-CyD is shown in Table 2 by taking the solubility without addition of β-CyD as 1.

TABLE 2

| β-CyD (mg) | Solubility |
|---|---|
| 0 | 1.0 |
| 20 | 3.1 |

EXAMPLE 3

Five milligrams of 6-O-(N-chloroacetylcarbamoyl)-fumagillol was added to 20 mg of β-CyD, dimethyl-β-CyD, 2-hydroxyethyl-β-CyD or 2,3-dihydroxypropyl-β-CyD dissolved in distilled water (1 ml), and the mixture was stirred at room temperature (15 to 25° C.). After 4 hours, the mixture was filtered through a filter (0.22 μm in pore diameter) and the fumagillol compound obtained in the filtrate was quantitatively determined by HPLC.

Solubility upon addition of CyD is shown in Table 3 by taking the solubility without addition of CyD as 1.

TABLE 3

| CyD (mg) | Solubility |
|---|---|
| without addition | 1.0 |
| β-CyD | 2.7 |
| DM-β-CyD | 2.8 |
| 2-HE-β-CyD | 2.7 |
| 2,3-DHP-β-CyD | 2.7 |

Note)
DM: dimethyl
HE: hydroxyethyl
DHP: dihydroxypropyl

EXAMPLE 4

Ten milligrams of 1-benzylmethylsulfonylmethyl-4-O-(N-chloroacetylcarbamoyl)-2-(1,2-epoxy-1,5-dimethyl-4-hexenyl-5-methoxy-1,4-cyclohexanediol bromide was added to 20 mg of β-CyD dissolved in distilled water (1 ml), and the mixture was stirred at room temperature (15 to 25° C.). After 4 hours, the mixture was filtered through a filter (0.22 μm) in pore diameter) and the bromide compound obtained in the filtrate was quantitatively determined by HPLC.

Solubility upon addition of β-CyD is shown in Table 4 by taking the solubility without addition of β-CyD as 1.

TABLE 4

| β-CyD (mg) | Solubility |
|---|---|
| 0 | 1.0 |
| 20 | 1.8 |

EXAMPLE 5

One hundred milligrams of 4-(N-chloroacetylcarbamoyloxy)-2-(1,2-epoxy-1,5-dimethyl-4-hexenyl)-(1,3-dihydrobenzo[C]thiophen-2-ylio)-3-methoxycyclohexanol chloride was added to 300 mg of 2-hydroxyethyl-β-CyD dissolved in distilled water (1 ml) and the mixture was stirred at room temperature (15 to 25° C.). After 4 hours, the mixture was filtered through a filter (0.22 μm in pore diameter) and the chloride compound obtained in the filtrate was quantitatively determined by HPLC.

Solubility upon addition of 2-hydroxyethyl-β-CyD is shown in Table 5 by taking the solubility without addition of 2-hydroxyethyl-β-CyD as 1.

TABLE 5

| 2HE-β-CyD (mg) | Solubility |
|---|---|
| 0 | 1.0 |
| 300 | 1.3 |

EXAMPLE 6

A cell suspension of mouse reticulum cell sarcoma M5076 ($2 \times 10^6$ cells) was subcutaneously implanted in female C57BL/6 mice. A solution of the complex of 6-O-(N-chloroacetylcarbamoyl)fumagillol (hereinafter abbreviated as the compound a) and β-CyD (compound a/β-CyD =⅓, by weight) in physiological saline was subcutaneously administered ten times at a site separated from the tumor implanted site during 12 days from the next day of the implantation. After 13 days, the volume of the tumor [length×(width/2)$^2$] was measured and expressed by the ratio to the volume of the control group (T/C). A suspension of the compound a in 5% gum arabic-physiological saline (containing 1% ethanol) was administered as the control.

Further, the suspension of the above compound a and an aqueous solution of the complex β-CyD were orally administered to the rat suffering from cancer implanted in according to the same manner, and carcinostatic effect was evaluated.

The results are shown in Table 6.

TABLE 6

| | Subcutaneous administration | | | Oral administration | | |
|---|---|---|---|---|---|---|
| Sample | Number | Dose of Compound a (mg/kg/day) | T/C (%) | Number | Dose of Compound a (mg/kg/day) | T/C (%) |
| Control | 12 | 0 | 100 | 11 | 0 | 100 |
| suspension | 6 | 3 | 47 | 6 | 10 | 86 |
| | 6 | 10 | 27 | 6 | 30 | 65 |
| | | | | 6 | 45 | 45 |
| Control | 11 | 0 | 100 | 11 | 0 | 100 |
| β-CyD | 6 | 3 | 33 | 6 | 10 | 83 |
| Aq. soln. of the complex | 6 | 10 | 19 | 4 | 30 | 56 |
| | | | | 5 | 45 | 28 |

The aqueous solution of the complex of the compound a and β-CyD manifests greater carcinostatic effect by both subcutaneous and oral administrations in comparison with the suspension of the compound a in gum arabic. This result suggests that the compound a and β-CyD form a complex to improve solubility, resulting in promotion of absorption and manifestation of greater pharmacological activity.

On the other hand, according to the present invention, the above fumagillol (I) or a salt thereof can be formulated as an aqueous solution thereof, enabling intravascular administration at a higher dose.

EXAMPLE 7

Five milligrams of 6-O-(N-chloroacetylcarbamoyl)-fumagillol was added to 10 or 20 mg of 6-O-α-maltosyl-β-CyD ($G_2$-β-CyD) dissolved in distilled water (1 ml), and the mixture was stirred at room temperature (15 to 25° C.). After 4 hours, the mixture was filtered through a filter (0.22 μm in pore diameter) and the fumagillol compound obtained in the filtrate was quantitatively determined by HPLC.

Solubility upon addition of $G_2$-β-CyD is shown in Table 7 by taking the solubility without addition of $G_2$-β-CyD as 1.

TABLE 7

| $G_2$-β-CyD (mg) | Solubility |
|---|---|
| 0 | 1.0 |
| 10 | 2.4 |
| 20 | 2.8 |

EXAMPLE 8

Five milligrams of 6-O-(N-chloroacetylcarbamoyl)-fumagillol and the equimolar amount of α- or β-CyD were added to distilled water (3 ml), and the mixture was stirred at room temperature (15 to 25° C.). After 4 hours, the mixture was filtered through a filter (0.22 μm in pore diameter) and lyophilized. The resulting lyophilized product was dissolved in heavy water and analyzed by $^1$H-NMR. The results are shown in Table 8.

TABLE 8

| | δ (ppm) | | |
|---|---|---|---|
| Proton | Nothing added | α-CyD added | β-CyD added |
| 8 | 1.07 | 1.06 | 1.08 |
| 1'-Me | 1.18 | 1.19 | 1.24 |
| 6'a | 1.63 | 1.68 | 1.64 |
| 6'b | 1.72 | 1.75 | 1.72 |
| 4 | 1.93 | 1.94 | 1.93 |
| 8,7,7,3' | 1.7–2.3 | 1.7–2.3 | 1.7–2.32 |
| 3' | 2.35 | 2.30 | 2.60 |
| 2 | 2.73 | 2.76 | 2.78 |
| 2' | 2.86 | 2.87 | 2.74 |
| 2 | 3.06 | 3.05 | 3.08 |
| OMe | 3.41 | 3.40 | 3.43 |
| 5 | 3.83 | | |
| CH$_2$ | 4.36 | 4.38 | 4.38 |
| 4' | 5.23 | 5.29 | 5.18 |
| 6 | 5.58 | 5.58 | 5.61 |

When α-CyD was added, signals of 3∝, 4' and 6'a protons were shifted and interaction between such moieties and α-CyD was observed.

When β-CyD was added, signals of 1'-Me, 2', 3' and 4' protons were shifted. The signals of 2' and 3' protons closely agreed with those in chloroform-d. Thus, inclusion of these protons by β-CyD and interaction between 1'-Me and 4' protons and βCyD were observed.

EXAMPLE 9

The filtrate obtained in Example 4 was lyophilized. The resulting lyophilized product was dissolved in heavy water and analyzed by $^1$H-NMR. The results are shown in Table 9.

TABLE 9

| | δ (ppm) | |
|---|---|---|
| Proton | Without addition | β-CyD added |
| 1'-Me | 1.37 | 1.45 |
| 1'-Me | 1.38 | 1.45 |
| 6'a | 1.62 | 1.64 |
| 6'b | 1.68 | 1.72 |
| 3' | 2.47 | 2.65 |
| S-Me | 2.78 | 2.78 |
| S-Me | 2.93 | 2.97 |
| OMe | 3.31 | 3.34 |
| OMe | 3.33 | 3.36 |

TABLE 9-continued

| Proton | δ (ppm) | |
|---|---|---|
| | Without addition | β-CyD added |
| COCH$_2$Cl | 4.34 | 4.37 |
| 4' | 5.13 | 5.13 |
| 6 | 5.44 | 5.47 |

Signals of 1'-Me and 3' protons were shifted and interaction between such portions and β-CyD was observed.

As described hereinabove, the complex of the present invention is readily soluble in water and manifests strong antineoplastic activity.

We claim:

1. A complex of a fumagillin derivative represented by the formula:

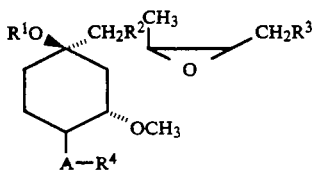

wherein $R^1$ is hydrogen; $R^2$ is halogen, $N(O)_mR^5R^6$, $N^+R^5R^6R^7 \cdot X^-$, $S(O)_nR^5$ or $S^+R^5R^6 \cdot X^-$ (wherein $R^5$, $R^6$ and $R^7$ are independently an optionally substituted hydrocarbon or heterocyclic group; $X^-$ is a counter anion; m is an integer of 0 or 1; n is an integer from 0 to 2; and $R^5$ and $R^6$ together with the adjacent nitrogen or sulfur atom may form a nitrogen- or sulfur-containing heterocyclic group which may be substituted and form a condensed ring); or $R^1$ and $R^2$ together represent a bond; $R^3$ is 2-methyl-1-propenyl group or isobutyl group; A is O or $NR^8$ (wherein $R^8$ is hydrogen or an optionally substituted lower alkyl or aryl group); $R^4$ is hydrogen, an optionally substituted hydrocarbon group or an optionally substituted acyl group with the proviso that when $R^1$ and $R^2$ together represent a bond and $R^3$ is —CH=C(CH$_3$)$_2$ then A—$R^4$ is not —OOC(CH=CH)$_4$COOH; or a salt thereof, with a cyclodextrin or etherified cyclodextrin.

2. A complex according to claim 1, wherein the fumagillin derivative is 6-O-(N-chloroacetylcarbamoyl)-fumagillol.

3. A complex according to claim 1, wherein the fumagillin derivative is 6α-O-(N'-chloroacetylureido)-6-desoxyfumagillol.

4. A complex according to claim 1, wherein the fumagillin derivative is 1-benzylmethylsulfonylmethyl-4-O-(N-chloroacetylcarbamoyl)-2-(1,2-epoxy-1,5-dimethyl-4-hexenyl)-5-methoxy-1,4-cyclohexanediol bromide.

5. A complex according to claim 1, wherein the fumagillin derivative is 4-(N-chloroacetylcarbamoyloxy)-2-(1,2-epoxy-1,5-dimethyl-4-hexenyl)-1-(1,3-dihydrobenzo[C]-thiophen-2-ylio)-3-methoxycyclohexanol chloride.

6. A complex according to claim 1, wherein the hydrocarbon group is a straight or branched chain $C_{1-6}$ alkyl, $C_{2-6}$ alkenyl, $C_{2-6}$ alkynyl, $C_{3-6}$ cycloalkyl, $C_{3-6}$ cycloalkenyl, $C_{7-13}$ aralkyl or $C_{6-10}$ aryl group.

7. A complex according to claim 1, wherein the heterocyclic group is a 5- or 6-membered heterocyclic group containing 1 to 4 hetero atoms selected from N, O and S.

8. A complex according to claim 1, wherein the nitrogen-containing heterocyclic group is a 4- to 7-membered nitrogen-containing heterocyclic group.

9. A complex according to claim 1, wherein the sulfur-containing heterocyclic group is a 4- to 7-membered sulfur-containing heterocyclic group.

10. A complex according to claim 1, wherein the lower alkyl is a $C_{1-6}$ alkyl group.

11. A complex according to claim 1, wherein the aryl group is a $C_{6-10}$ aryl group.

12. A complex according to claim 1, wherein the acyl group is a $C_{1-6}$ alkanoyl, $C_{7-11}$ aroyl, a 5- or 6-membered heterocyclic carbonyl containing 1 to 4 hetero atoms selected from N, O and S, Carbamoyl, thiocarbamoyl, $C_{6-10}$ arylsulfonyl, $C_{1-6}$ alkylsulfonyl, sulfamoyl, $C_{2-7}$ alkoxycarbonyl or $C_{7-11}$ aryloxycarbonyl.

13. A complex according to claim 1, wherein the hydrocarbon, heterocyclic, nitrogen- or sulfur-containing heterocyclic, lower alkyl, aryl or acyl group may be substituted with 1 to 3 substituents selected from the group consisting of a $C_{1-6}$ alkyl; $C_{2-6}$ alkenyl, $C_{2-6}$ alkynyl, $C_{3-6}$ cycloalkyl, $C_{3-6}$ cycloalkenyl, $C_{6-10}$ aryl, amino, $C_{1-6}$ alkylamino, di-$C_{1-6}$ alkylamino, azido, nitro, halogen, hydroxyl, $C_{1-4}$ alkoxy, $C_{6-10}$ aryloxy, $C_{1-6}$ alkylthio, $C_{6-10}$ arylthio, cyano, carbamoyl, carboxyl, $C_{1-4}$ alkoxycarbonyl, $C_{7-11}$ aryloxycarbonyl, carboxy-$C_{1-4}$ alkoxy, $C_{1-6}$ alkanoyl, $C_{7-10}$ aroyl, $C_{6-10}$ arylsulfonyl, $C_{1-6}$ alkylsulfinyl, $C_{6-10}$ arylsulfinyl, $C_{1-6}$ alkylsulfonyl, 5- or 6-membered heterocyclic group containing 1 to 4 hetero atoms selected from N, O and S, 5- or 6-membered heterocyclic carbonyl containing 1 to 4 hetero atom selected from N, O and S, or 5- or 6-membered heterocyclic thio containing 1 to 4 hetero atoms selected from N, O and S which may be condensed with benzene ring; the substituent having optionally further 1 to 3 substituents selected from a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-10}$ aryl group, amino, $C_{1-6}$ alkylamino group, di-$C_{1-6}$ alkylamino group, azido, nitro, halogen, hydroxyl, $C_{1-4}$ alkoxy group, $C_{6-10}$ aryloxy group, $C_{1-6}$ alkylthio group, $C_{6-10}$ arylthio group, cyano, carbamoyl, carboxyl, $C_{1-4}$ alkoxylcarbonyl group, $C_{7-11}$ aryloxycarbonyl group, carboxy-$C_{1-4}$ alkoxy group, $C_{1-6}$ alkanoyl group, $C_{7-11}$ aroyl group, $C_{6-10}$ arylsulfonyl group, $C_{1-6}$ alkylsulfinyl group, $C_{6-10}$ arylsulfinyl group, $C_{1-6}$ alkylsulfonyl group, 5- or 6-membered heterocyclic group containing 1 to 4 hetero atoms selected from N, o and S, 5- or 6-membered heterocyclic carbonyl group containing 1 to 4 hetero atoms selected from N, O and S and 5- or 6-membered heterocyclic thio group containing 1 to 4 hetero atoms selected from N, O and S which may be condensed with benzene ring.

14. A complex according to claim 1, wherein the substituted acyl group is a disubstituted carbamoyl, thiocarbamoyl or sulfamoyl group, the substituents together with the nitrogen atom forming a nitrogen-containing heterocyclic group.

15. A complex according to claim 1, wherein $R^1$ is hydrogen; $R^2$ is a 4- to 7-membered sulfur-containing heterocyclic group which may be condensed with benzene, pyridine, pyrazine, pyridazine or cyclohexane; or $R^1$ and $R^2$ together represent a bond; $R^3$ is 2-methyl-1-propenyl; A is O or NH; and $R^4$ is an optionally substituted carbamoyl group.

16. A complex according to claim 15, wherein the 4- to 7-membered sulfur-containing heterocyclic group which may be condensed is 1,3-dihydrobenzo[C]thiophen-2-yl group.

17. A complex according to claim 15, wherein a substituent in the optionally substituted carbamoyl group is a halogen-$C_{1-6}$ alkanoyl group.

18. A complex according to claim 15, wherein the optionally substituted carbamoyl group is N-chloroacetylcarbamoyl group.

19. A complex according to claim 1, wherein the cyclodextrin or etherified cyclodextrin is a compound of the formula:

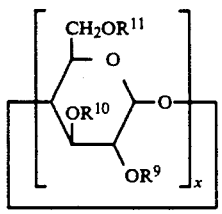

wherein x is an integer of 6 to 12; and $R^9$, $R^{10}$ and $R^{11}$ are independently hydrogen, $C_{1-4}$ alkyl, monohydroxy-$C_{1-4}$-alkyl, dihydroxy-$C_{1-4}$-alkyl, carboxy-$C_{1-4}$-alkyl or a sugar residue, and $R^9$, $R^{10}$ and $R^{11}$ in respective repetition units are the same or different.

20. A complex according to claim 1, wherein an amount of the optionally etherified cyclodextrin is in the ratio of 1/10 to 50 times by weight to that of the fumagillin derivative or a salt thereof.

21. A complex according to claim 1, wherein the optionally etherified cyclodextrin is 2-hydroxyethyl-$\beta$-cyclodextrin.

22. A complex according to claim 1, wherein includes a free fumagillol derivative, a salt thereof and/or a free optionally etherified cyclodextrin.

23. An antineoplastic composition which comprises a complex of a fumagillin derivative represented by the formula:

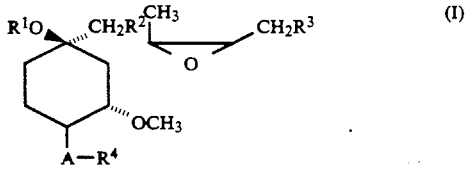

wherein $R^1$ is hydrogen; $R^2$ is halogen, $N(O)mR^5R^6$, $N^+R^5R^6R^7 \cdot X^-$, $S(O)NR^5$ or $S^+R^5R^6 \cdot X^-$ (wherein $R^5$, $R^6$ and $R^7$ are independently an optionally substituted hydrocarbon or heterocyclic group; $X^-$ is a counter anion; m is an integer of 0 or 1; n is an integer from 0 to 2; and $R^5$ and $R^6$ together with the adjacent nitrogen or sulfur atom may form a nitrogen- or sulfur-containing heterocyclic group which may be substituted and form a condensed ring); or $R^1$ and $R^2$ together represent a bond; $R^3$ is 2-methyl-1-propenyl group or isobutyl group; A is O or $NR^8$ (wherein $R^8$ is hydrogen or an optionally substituted lower alkyl or aryl group); $R^4$ is hydrogen, an optionally substituted hydrocarbon group or an optionally substituted acyl group with the proviso that when $R^1$ and $R^2$ together represent a bond and $R^3$ is —CH=C(CH$_3$)$_2$ then A—$R^4$ is not —OOC(CH=CH)$_4$COOH; or a salt thereof, with a cyclodextrin or etherified cyclodextrin.

24. An antineoplastic composition according to claim 23, wherein the fumagillin derivative is 6-O-(N-chloroacetylcarbamoyl)-fumagillol.

25. An antineoplastic composition according to claim 23, wherein the fumagillin derivative is 6α-O-(N'-chloroacetylureido)-6-desoxyfumagillol.

26. An antineoplastic composition according to claim 23, wherein the fumagillin derivative is 1-benzylmethylsulfonylmethyl-4-O-(N-chloroacetylcarbamoyl)-2(1,2-epoxy-1,5-dimethyl-4-hexenyl)-5-methoxy-1,4-cyclohexanediol bromide.

27. An antineoplastic composition according to claim 23, wherein the fumagillin derivative is 4-(N-chloroacetylcarbamoyloxy)-2-(1,2-epoxy-1,5-dimethyl-4-hexenyl)-(1,3-dihydrobenzo[C]-thiophen-2-ylio)-3-methoxycyclohexanol chloride.

28. A method for providing antineoplastic activity for a patient requiring such an activity comprising administering thereto an effective amount of a complex of a fumagillin derivative represented by the formula:

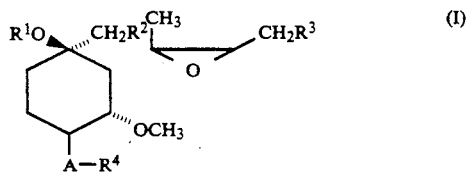

wherein $R^1$ is hydrogen; $R^2$ is halogen, $N(O)mR^5R^6$, $N^+R^5R^6R^7 \cdot X^-$, $S(O)NR^5 S^+R^5R^6 \cdot X^-$ (wherein $R^5$, $R^6$ and $R^7$ are independently an optionally substituted hydrocarbon or heterocyclic group; $X^-$ is a counter anion; m is an integer or 0 or 1; n is an integer from 0 to 2; and $R^5$ and $R^6$ together with the adjacent nitrogen or sulfur atom may form a nitrogen- or sulfur-containing heterocyclic group which may be substituted and form a condensed ring); or $R^1$ and $R^2$ together represent a bond; $R^3$ is 2-methyl-1-propenyl group or isobutyl group A is O or $NR^8$ (wherein $R^8$ is hydrogen or an optionally substituted lower alkyl or aryl group); $R^4$ is hydrogen, an optionally substituted hydrocarbon group or an optionally substituted acyl group with the proviso that when $R^1$ and $R^2$ together represent a bond and $R^3$ is —CH=CH(CH$_3$)$_2$ then A—$R^4$ is not —OOC(CH=CH)$_4$COOH; or a salt thereof, with a cyclodextrin or etherified cyclodextrin.

29. A method according to claim 28, wherein the fumagillin derivative is 6-O-(N-chloroacetylcarbamoyl)fumagillol.

30. A method according to claim 28, wherein the fumagillin derivative is 6α-O-(N'-chloroacetylureido)-6-desoxyfumagillol.

31. A method according to claim 28, wherein the fumagillin derivative is 1-benzylmethylsulfonylmethyl-4-O-(N-chloroacetylcarbamoyl)-2-(1,2-epoxy-1,5-dimethyl-4-hexenyl)-5-methoxy-1,4-cyclohexanediol bromide.

32. A method according to claim 28, wherein the fumagillin derivative is 4-(N-chloroacetylcarbamoyloxy)-2-(1,2-epoxy-1,5-dimethyl-4-hexenyl)-(1,3-dihydrobenzo[C]-thiophen-2-ylio)-3-methoxycyclohexanol chloride.

* * * * *

UNITED STATES PATENT AND TRADEMARK OFFICE
CERTIFICATE OF CORRECTION

PATENT NO. : 5,196,406
DATED : March 23, 1993
INVENTOR(S) : Kamei, et. al.

It is certified that error appears in the above-indentified patent and that said Letters Patent is hereby corrected as shown below:

In each of the following instances:

Cover page, in the Abstract,

Column 1, lines 55-62,

Column 11, lines 20-25,

Column 13, lines 42-49,

Column 14, lines 24-30,

Signed and Sealed this

Twenty-seventh Day of August, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,196,406
DATED : March 23, 1993
INVENTOR(S) : Kamei, et. al.

It is certified that error appears in the above-indentified patent and that said Letters Patent is hereby corrected as shown below:

Please replace " 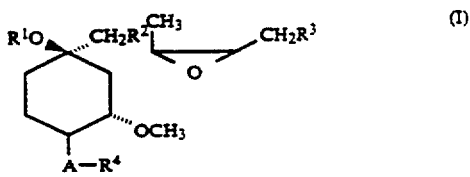 " (I)

With -- 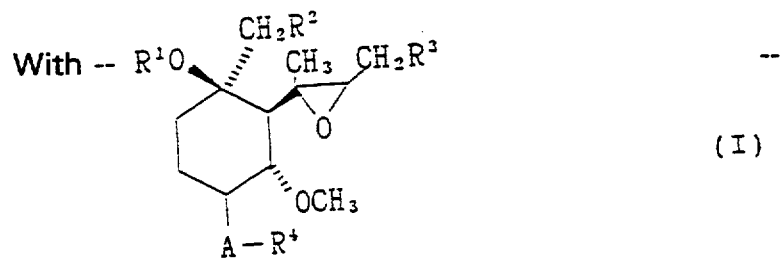 -- (I)